United States Patent [19]
Bruninx

[11] 4,131,794
[45] Dec. 26, 1978

[54] FLUORESCENT X-RAY SPECTROMETER

[75] Inventor: Edward Bruninx, Eindhoven, Netherlands

[73] Assignee: U.S. Philips Corporation, New York, N.Y.

[21] Appl. No.: 743,648

[22] Filed: Nov. 22, 1976

[30] Foreign Application Priority Data
Nov. 25, 1975 [NL] Netherlands ............ 7513716

[51] Int. Cl.² ............................................. G01N 23/20
[52] U.S. Cl. ............................................. 250/272; 250/280
[58] Field of Search ............ 250/272, 273, 274, 275, 250/276, 280, 370, 385

[56] References Cited
U.S. PATENT DOCUMENTS

| | | |
|---|---|---|
| 3,321,624 | 5/1967 | Kishino et al. ............ 250/272 X |
| 3,354,308 | 11/1967 | Engel et al. ............ 250/272 |
| 4,031,396 | 6/1977 | Whetten et al. ............ 250/385 |

*Primary Examiner*—Davis L. Willis
*Attorney, Agent, or Firm*—Thomas A. Briody

[57] ABSTRACT

A location-sensitive detector which can be read on-line is included in a fluorescent X-ray spectrometer comprising an analyzing crystal. Thus, the analysis result can be directly displayed and recorded without a film density measurement being required. For the detector use can be made of, for example, a gas-filled counter comprising a properly defined collector wire, a solid-state detector consisting of a row of detection elements, or a high-pressure camera which comprises electrodes which are constructed to be selective.

7 Claims, 5 Drawing Figures

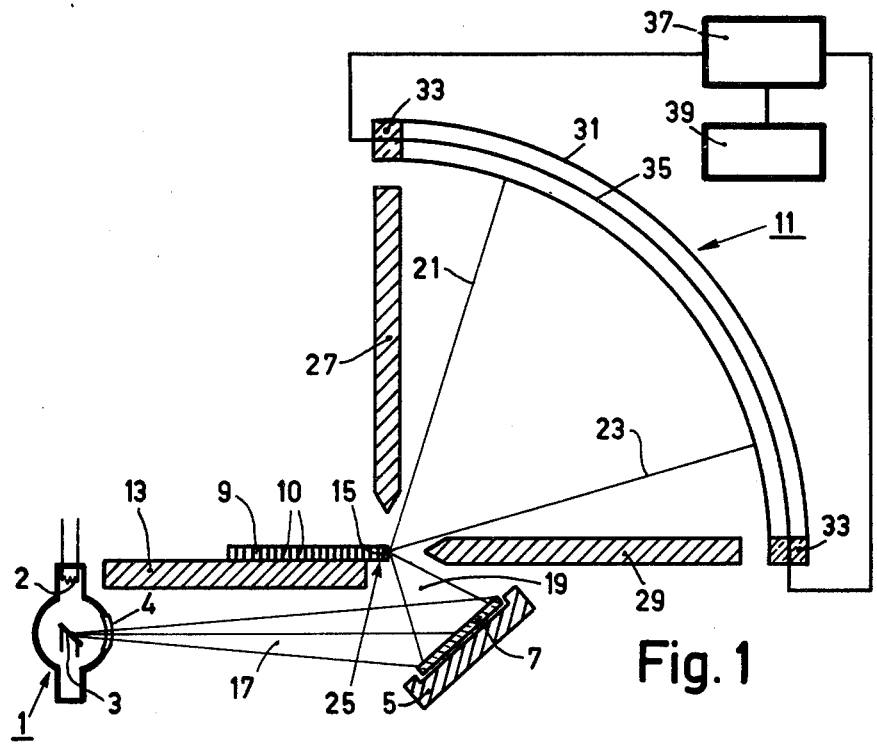
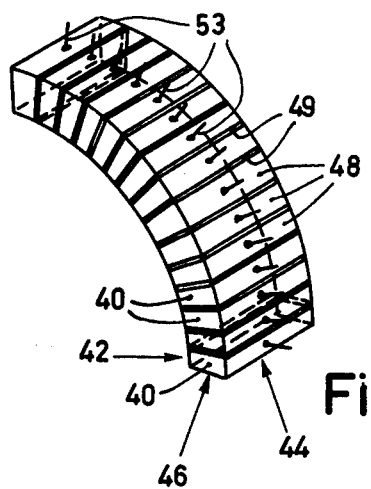
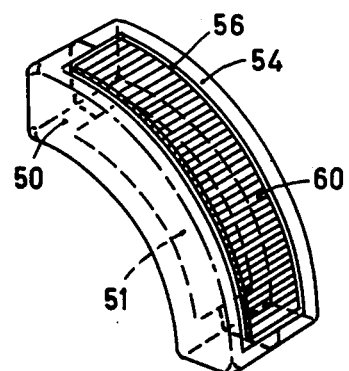
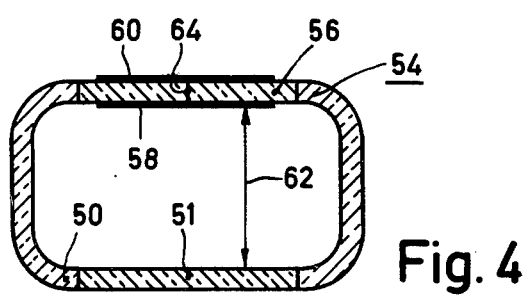
Fig. 1
Fig. 2
Fig. 3
Fig. 4

FLUORESCENT X-RAY SPECTROMETER

The invention relates to a fluorescent X-ray spectrometer, comprising an X-ray source, a radiation detector and an analyzing crystal which is arranged so that wavelength dispersion occurs and X-radiation of a given wavelength coincides at least substantially with a line transversely of the dispersion direction on the detector.

A spectrometer of this kind is known, for example, from United States Patent No. 2,842,670. The detector of the spectrograph described therein is formed by a photographic film, the local density of which must be measured, for example, by means of a densitometer after the entire analysis has been completed. The detector may alternatively be formed by a counter which scans the measuring field during the measurement.

The location of the density of the film is then characteristic of the elements present in a specimen to be analyzed. A drawback of a spectrograph utilizing a film as the detector consists in that the detection does not permit on-line measurement. This means that each measurement must be completed before the result can be determined from the measurement of the film density. The specimen will meanwhile have been replaced by another specimen in many cases, and a further determination, if desired, cannot be performed, so that a completely new measurement is required. Consequently, the entire measurement is rather time consuming. There is further practical drawback in that the film must be very accurately installed in the apparatus or a reference must be recorded on each film. Distortion in the longitudinal direction of the film can also adversely affect the measuring accuracy. A spectrometer in which the detector scans the measuring field has the drawback that the registration of the position of the detector during the measurement is decisive for the measuring accuracy. This requires a comparatively expensive displacement mechanism for the detector.

The invention has for its object to eliminate these drawbacks; to this end, a fluorescent X-ray spectrometer of the kind set forth according to the invention is characterized in that the radiation detector is rigidly arranged in the spectrometer and can be read in a location-dependent and on-line manner. The analyzing crystal of the invention is disposed such that at least an end face thereof is exposed to X-radiation from the specimen, it being possible for such end face and a portion of a side or principal face of the analyzing crystal to be so exposed along with the end face.

As a result of the use of a rigidly arranged, on-line readable, location-sensitive detector, the measuring values of a specimen can be directly evaluated, i.e. during the measurement, without parts which move during the measurement being included in the spectrometer. As a result, any further measurements can be directly performed. In comparison with a simultaneously operating spectrograph comprising detectors without analyzing crystal, better resolution is achieved.

For the location-sensitive detector use can be made of, for example, a gas-filled counter as described in The Rev. of Scientific Instruments, Vol. 39 (1968), No. 10, pages 1515–1522. Other location-sensitive detectors such as a Silicon detector or a high-pressure camera can alternatively be used. A location-sensitive detector of this kind can be constructed to be homogeneous in the dispersion direction, but may also be composed of a row of individually readable detectors, each of which has a comparatively small dimension in the dispersion direction of the radiation to be measured.

Some preferred embodiments of a spectrometer in accordance with the invention will be described in detail hereinafter with reference to the accompanying diagrammatic drawing.

FIG. 1 is a diagrammatic view of a spectrometer in accordance with the invention, comprising a detector in the form of a gas-filled counter, and FIGS. 2, 3 and 4 show embodiments of further detectors.

Figure 5:
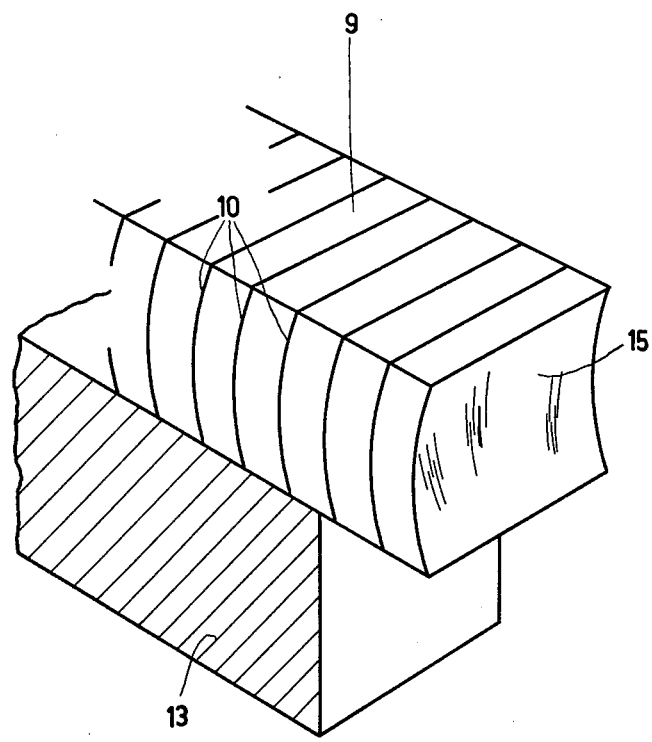
FIG. 5 depicts an embodiment of the invention, comprising a curved analyzing crystal.

The drawing shows the following items of a spectrometer: an X-ray source 1 with a filament 2, an anode 3, and an exit window 4, a specimen 7 on a specimen carrier 5, an analyzing crystal 9 with crystal faces 10, and a detector 11. The radiation of the X-ray source 1 can be chromatized by utilizing suitable windows or filters.

The analyzing crystal 9 may be disposed relative to a shielding plate 13 so that only an end face 15 of the crystal is exposed to X-radiation i.e., fluorescent radiation, from the specimen. On the end face 15 fluorescent radiation 19, produced by an X-ray beam 17 from the X-ray source 1, is diffracted in known manner and hence dispersed in dependence of the wavelength characteristic of each element present in the specimen. In the drawing there are two diffraction directions (21 and 23), i.e. directions for two wavelengths occurring in the fluorescent radiation. If only the end face 15 of the crystal is effectively used, a comparatively high resolution can be achieved because little wavelength-independent, and hence undesired, spreading occurs in the diffracted radiation, but the signal to be detected is comparatively weak. It is to be noted that the dimension of the crystal, measured transversely of the shielding plate 13, for example, approximately 0.1 mm. A stronger signal can be obtained by making the crystal project beyond the plate 13 so that, as is shown in the drawing, a portion 25 of a side face is also exposed to radiation and hence also transmission diffraction occurs. A larger undesired spreading of the diffracted radiation then occurs. Consequently, a favourable dimension of the flat crystal portion projecting beyond the plate 13 is determined on the basis of a compromise between the resolution on the one hand and the signal intensity on the detector on the other hand. A practical value for the crystal shown here is, for example, approximately 1 mm. In a further preferred embodiment, the analyzing crystal 9 (FIG. 5) is curved so that due to the orientation of the crystal faces 10 a monochromatic X-ray beam which is incident thereon is diffracted to form a beam which, viewed in the dispersion direction, is focussed on the detector. The signal to be detected can thus be amplified without reduction of the resolution. In order to prevent the radiation from reaching the detector 11 directly from the specimen or even from the source, besides the shielding plate 13, further plates 27 and 29 which shield the beam laterally are arranged between the specimen and the detector in a preferred embodiment. These shielding plates 13, 27, 29, are preferably made of a material having a high atomic number, for example, lead.

The detector in the present embodiment consists of a curved, gas-filled counter. This counter comprises a suitably homogeneous collector wire having a given resistance and capacitance per unit of length, for example as described in the above article in Review of Scientific Instruments Vol 39. For a suitable adaptation of the detector to the geometry of the spectrograph, it is curved, in this case an arc of approximately 90° with a radius of curvature of approximately 20 cm. The housing 31 of such a counter consists of, for example, a tube which is closed on both ends by electrically insulating plugs 33 which also serve as passages for a collector wire 35, for example, consisting of a carbon wire. On the side which faces the analyzing crystal, the tube comprises a radiation window, for example, made of beryllium or aluminized mylar foil. In order to ensure suitable central positioning of the collector wire for a prolonged period of time, it is subjected to a preliminary operation during which a permanent bent shape is impressed. The wire can alternatively be positioned by local supports. Disturbances of the potential distribution in the counter must then be avoided, for example, by optimum adaptation of the supports to the existing field. For the location-dependent reading of the detector, use can be made of a suitable known electronic circuit 37 which comprises, for example, an energy analyzer and provides multi-channel analysis.

A further preferred embodiment utilizes for the detection a solid-state detector consisting of a single row of detector elements which can be separately read by a known circuit which receives per detector element the signals to be recorded. Detectors of this kind with appropriate read circuits are also known per se, be it perhaps without a curved shape.

Because the resolution is in this case determined by the dimension of the detector elements, the detector need not be curved. For a straight row of detectors, a difference in distance can be compensated for electronically. As is shown in FIG. 2, a detector of this kind is composed, for example, of elements 40 which have a dimension 42 in the dispersion direction of, for example, 1 mm, a dimension 44 in the direction transverse thereto of, for example, from 10 to 20 mm, and a dimension 46 in the direction of the beam path which is adapted to the penetration depth of the relevant radiation. Each of the detection elements 40 comprises a read connection 53. Intermediate spaces 49 between the detection elements can be filled with an electrically insulating material which also has a high absorption factor for the radiation to be detected.

The detector of a further preferred embodiment consists of an adapted high-pressure camera of the type described for other purposes in United States Patent No. 3,774,029. As is shown in FIG. 3, this camera is constructed as a flat, curved tube having a wall 50 which faces the analyzing crystal and which comprises an electrically conductive window 51 adapted to the X-radiation occurring. A portion 56 of an opposite wall 54 is provided with electrodes on the inner as well as the outer side. Each of the inner electrodes 58 is connected through the wall 54 to a corresponding electrode 60 on the outer side. Therefore, the wall portion 56 provided with the electrodes 58, 60 is made, for example, of an insulating material such as glass, synthetic material or ceramic material, with built-in electrical passages which are directed transversely of the surfaces. The mutually insulated inner electrodes have dimensions which correspond, for example, to those of the individual detection elements of the detector shown in FIG. 2, whilst the distance 62 between the front wall and the rear wall is again adapted to the radiation to be detected and amounts to, for example, approximately 10 mm. Due to the high gas pressure, this distance may be smaller than that in the gas-filled counter, so that deviations in the geometry have a less severe effect on the resolution. All outer electrodes 60 are again provided with connections 64 for supplying signals to be recorded to electronic circuits (not shown).

What is claimed is:

1. A fluorescent X-ray spectrometer for analyzing a specimen, comprising an X-ray source, a radiation detector and an analyzing crystal which comprises side faces and end faces, said analyzing crystal being arranged so that wavelength dispersion occurs and X-radiation of a given wavelength coincides at least substantially with a line transversely to the dispersion direction of the detector, said radiation detector being rigidly arranged in the spectrometer and being readable in a location-dependent and on-line manner, said X-ray source being located so as to direct X-rays to said specimen to produce fluorescent radiation and said analyzing crystal being located so that at least a said end face is exposed to and diffracts said fluorescent radiation, said radiation detector receiving said radiation from said analyzing crystal.

2. A fluorescent X-ray spectrometer as in claim 1, wherein said end face of said analyzing crystal extends parallel to crystal faces of the crystal.

3. A fluorescent X-ray spectrometer as in claim 1, wherein a comparatively small part of a surface of said analyzing crystal which extends transversely to the crystal faces of said crystal can be irradiated by said fluorescent radiation.

4. A fluorescent X-ray spectrometer as in claim 1, wherein that portion of said analyzing crystal irradiated by said fluorescent radiation is curved so that diffracted radiation of a given wavelength is incident on the detector in an at least substantially line-shaped focus.

5. A fluorescent X-ray spectrometer as in claim 1, wherein said detector consists of a row of solid state detector elements which can be separately read.

6. A fluorescent X-ray spectrometer as in claim 1, wherein said detector is constructed as an ionization chamber, which is bent through approximately 90° and contains a collector wire having a predetermined resistance and capacitance per unit of length.

7. A fluorescent X-ray spectrometer as in claim 1, wherein said detector consists of a high-pressure ionization chamber, bent through approximately 90°, whose potential field, generated by the radiation, can be externally detected in a location-dependent manner.

* * * * *